(12) United States Patent
Carvalho et al.

(10) Patent No.: US 9,737,478 B2
(45) Date of Patent: Aug. 22, 2017

(54) TREATMENT OF MALARIA (75) Inventors: Leonardo Jose de Moura Carvalho, La Jolla, CA (US); Pedro Cabrales, La Jolla, CA (US)

(73) Assignee: National Institutes of Health (NIH), U.S. Dept. of Health and Human Services (DHHS), The United States of America NIH Division of Extramural Inventions and Technology Resources (DEITR), Washington, DC (US)

( * ) Notice: Subject to any disclaimer, the term of this patent is extended or adjusted under 35 U.S.C. 154(b) by 517 days.

(21) Appl. No.: 12/881,124

(22) Filed: Sep. 13, 2010

(65) Prior Publication Data
US 2011/0077258 A1 Mar. 31, 2011

Related U.S. Application Data (60) Provisional application No. 61/246,507, filed on Sep. 28, 2009.

(51) Int. Cl.
| | |
|---|---|
| *A61K 9/00* | (2006.01) |
| *A61K 9/20* | (2006.01) |
| *A61K 9/28* | (2006.01) |
| *A61K 31/137* | (2006.01) |
| *A61K 31/155* | (2006.01) |
| *A61K 31/357* | (2006.01) |
| *A61K 31/4706* | (2006.01) |
| *A61K 31/4709* | (2006.01) |
| *A61K 31/49* | (2006.01) |
| *A61K 31/505* | (2006.01) |
| *A61K 45/06* | (2006.01) |
| *A61K 31/365* | (2006.01) |

(52) U.S. Cl.
CPC .......... *A61K 9/0019* (2013.01); *A61K 9/0004* (2013.01); *A61K 9/2004* (2013.01); *A61K 9/2806* (2013.01); *A61K 31/137* (2013.01); *A61K 31/155* (2013.01); *A61K 31/357* (2013.01); *A61K 31/365* (2013.01); *A61K 31/4706* (2013.01); *A61K 31/4709* (2013.01); *A61K 31/49* (2013.01); *A61K 31/505* (2013.01); *A61K 45/06* (2013.01)

(58) Field of Classification Search
CPC .. A61K 31/137; A61K 31/155; A61K 31/357; A61K 31/365; A61K 31/4706; A61K 31/4709; A61K 9/0004; A61K 9/0019; A61K 9/2004; A61K 9/2806; A61K 45/06
See application file for complete search history.

(56) References Cited

U.S. PATENT DOCUMENTS 4,406,906 A * 9/1983 Meyer et al. ................ 514/356
5,219,865 A * 6/1993 Chatterjee et al. .......... 514/305

OTHER PUBLICATIONS

Khaira et. al., Journal of the Association of Physicians of India, Sep. 2008, Association of Physicians: India, vol. 56, pp. 721-723.*
Bag et. al., Indian Pediatrics, 1994, Indian Academy of Pediatrics, vol. 31, pp. 821-825.*
http://medical-dictionary.thefreedictionary.com/unit+dose.*
http://medical-dictionary.thefreedictionary.com/parenteral.*
Childers et. al., The American Surgeon, 2003, ProQuest Central, vol. 69, issue 1, pp. 86-90.*
Beare et al. "Perfusion Abnormalities in Children With Cerebral Malaria and Malarial Retinopathy", J. Infect. Dis. 199(2):263-271, Jan. 15, 2009.
Choi et al., Drug Interaction Between Oral Atorvastatin and Verapamil in Healthy Subjects: Effects of Atorvastatin on the Pharmacokinetics of Verapamil and Norverapamil, Eur. J. Clin Pharmacol. 64:445-449, (2008).
Ciach et al., Reversal of Mefloquine and Quinine Resistance in Plasmodium falciparum with NP30, Antimicrobial Agents and Chemotherapy, pp. 2393-2396. Aug. 2003.
John et al., Cerebral Malaria in Children is Associated with Long-Term Cognitive Impairment, Pediatrics, (1):e92-99, Jul. 2008.
Kinoshita et al, An Autopsy Case of Combined Drug Intoxication Involving Verapamil, Metoprolol and Digoxin, Forensic Science International, 133:107-112 (2003).
Lackner et al, Behavioural and histopathological alterations in mice with cerebral malaria, Neuropathol Appl Neurobiol, (2006), 32:177-188.
Martins et al, Characterization of cerebral malaria in the outbred Swiss Webster mouse infected by plasmodium berghei anka, Int J Exp Pathol, (2009), 90:119-130.
Masseno et al., In Vitro Chemosensitization of Plasmodium falciparum to Antimalarials by Verapamil and Probenecid, Antimicrobial Agents and Chemotherapy, pp. 3131-3134, Jul. 2009.
McIntosh et al, Artemisinin derivatives for treating severe malaria (review), Cochrane Database Syst Rev, (2000), 2:CD000527.
Mostany et al., A method for 2-photon imaging of blood flow in the neocortex through a cranial window, Journal of Visualized Experiments, (12)pii:680, Feb. 15, 2008.
Newton et al, Perturbations of cerebral hemodynamics in Kenyans with cerebral malaria, Pediatr Neurol, (1996), 15:41-49.
Penet et al., Imaging Experimental Cerebral Malaria In Vivo: Significant Role of Ischemic Brain Edema, The Journal of Neuroscience, 25(32):7352-7358, Aug. 10, 2005.
Ranniger et al., Are One or Two Dangerous? Calcium Channel Blocker Exposure in Toddlers, Journal of Emegency Medicine, vol. 33, No. 2, pp. 145-154 (2007).
Rowe et al., The Burden of Malaria Mortality Among African Children in the Year 2000, International Journal of Epidemiology, 35(3):691-704 Jun. 2006.
Sanni et al., Is Ischemia Involved in the Pathogenesis of Murine Cerebral Malaria?, American Journal of Pathology, vol. 159, No. 3, Sep. 2001.
Schwalkwyk, et al., Quinoline-Resistance Reversing Agents for the Malaria Parasite Plasmodium Falciparum, Drug Resistance Updates 9, 211-226 (2006).
Shepherd, Treatment of Poisoning Caused by Beta-Adrenergic and Calcium-Channel Blockers, Am Jour Health-Sys Pharm, vol. 63, pp. 1828-1835, Oct. 1, 2006.

* cited by examiner

*Primary Examiner* — Sarah Pihonak
(74) *Attorney, Agent, or Firm* — Foley & Lardner LLP

(57) ABSTRACT

The invention contemplates compositions for the treatment of malaria comprising an anti-malaria drug and an adjuvant which promotes vasodilation and methods of using same.

3 Claims, 4 Drawing Sheets

TREATMENT OF MALARIA

RELATED APPLICATION

This application claims the benefit of U.S. Application No. 61/246,507, filed Sep. 28, 2009 which is hereby incorporated by reference herein in its entirety.

ACKNOWLEDGMENT

This invention was made with government support under Grant Nos. R01 HL087290 and R01 AI082610 awarded by the National Institutes of Health. The government has certain rights in the invention.

TECHNICAL FIELD

This invention relates to compositions for the treatment of malaria comprising an anti-malaria drug (e.g., artemether) and an adjuvant which promotes vasodilation (e.g., nimodipine) and methods of using same.

BACKGROUND

Malaria, a disease caused by protozoan parasites of the genus *Plasmodium*, is transmitted by the bite of *Anopheles* mosquitoes. Five species which cause disease in humans (*P. falciparum, P. vivax, P. malariae, P. ovale* and *P. knowlesi*) live and multiply first in hepatocytes (liver stage) then in red blood cells (blood stage). Each cycle of parasite multiplication lasts 48-72 hours and leads to the destruction of the host cell. It is manifested by symptoms like fever, headache, nausea, vomiting, diarrhea, prostration, chills. Left untreated, it may quickly develop into life-threatening complications such as cerebral malaria, severe anemia, acidosis, renal failure and pulmonary edema. There are other plasmodial species that infect hosts other than humans, such as *P. berghei*, that infects rodents.

Cerebral malaria, as defined by World Health Organization, is a clinical syndrome characterized by coma (inability to localize a painful stimulus) at least one hour after termination of a seizure or correction for hypoglycemia, detection of asexual forms of *P. falciparum* malaria parasites on peripheral blood smears and exclusion of other causes of encephalopathy. An unresolved issue of CM pathogenesis regards the role of brain hemodynamic perturbations and ischemia. Direct observation of retinal microvasculature shows impaired perfusion, vascular occlusion and ischemia (Beare, et al., *J Infect Dis.* 2009, 199, 263-271), whereas transcranial Doppler sonography shows normal or even increased cerebral blood flow (CBF) velocities in large arteries (Newton, et al., *Pediatr Neurol.* 1996, 1, 41-49).

Cerebral malaria (CM) caused by *Plasmodium falciparum* claims the lives of nearly 1 million children every year (Rowe, et al., *Int. J. Epidemiol.* 2006, 35, 691-704). Despite anti-malarial treatment, 10-20% of patients die and 1 in each 4 survivors develop neurological sequelae (McIntosh, et al., *Cochrane Database Syst. Rev.* 2000, 2, CD000527; John, et al. *Pediatrics.* 2008, 122, e92-99), therefore improved therapies are urgently needed.

SUMMARY OF THE INVENTION

It has been discovered that improved therapeutic effect for the treatment of malaria, especially CM, can be achieved using a combination of anti-malaria drug (e.g., artemether) and an adjuvant which promotes vasodilation (e.g., nimodipine).

DETAILED DESCRIPTION OF THE INVENTION

Various embodiments of the invention are described hereinafter. It should be noted that the specific embodiments are not intended as an exhaustive description of the invention or as a limitation on the scope of the invention. One aspect described in conjunction with a particular embodiment of the present invention is not necessarily limited to that embodiment and can be practiced with any other embodiment(s) of the invention.

In some embodiments, the present invention provides pharmaceutical compositions for the treatment of malaria, said composition comprising an anti-malaria drug, its pharmacologically acceptable salt, or a hydrate or solvate and an adjuvant which promotes vasodilation, its pharmacologically acceptable salt, or a hydrate or solvate.

There are several drugs that are able to kill plasmodial parasites and used to treat malaria. Exemplary anti-malarial drugs contemplated for use in the practice of the present invention include, but are not limited to, quinine, mefloquine, amodiaquine, chloroquine, halofantrine, atovaquone-proguanil, primaquine, sulfadoxine-pyrimethamine, artemisinin, its derivatives—artesunate, artemether, arteether, and the like.

In certain embodiments, the anti-malaria drug is selected from the group consisting of quinine (QN), mefloquine (MQ), amodiaquine, chloroquine (CQ), halofantrine, atovaquone-proguanil, primaquine, sulfadoxine-pyrimethamine, artemisinin, artemether, artesunate and arteether; preferably artemether.

As used herein, the term "adjuvant which promotes vasodilation" refers to a compound which, when administered in conjunction with an anti-malarial drug, is able to improve or accelerate recovery, and/or increase survival, of patients with malaria (especially cerebral malaria). It needs not enhance the parasite-killing activity of the anti-malarial drug. Its main purpose is to vasodilate the blood vessels or reduce contraction of the vascular smooth muscle so the blood can easily reach subject's brain. The adjuvant which promotes vasodilation used herein thus requires minimal and non-toxic amount.

In some embodiments, the adjuvant which promotes vasodilation is a vasodilator. The term "vasodilator" refers to any compound that can relax the smooth muscle in blood vessels, which causes the vessels to dilate. Dilation of arterial (resistance) vessels leads to a reduction in systemic vascular resistance, which leads to a fall in arterial blood pressure. Dilation of venous (capacitance) vessels decreases venous blood pressure. Exemplary vasodilators include, but are not limited to, calcium antagonists, alpha-blockers, angiotensin converting enzyme (ACE) inhibitors, angiotensin receptor blockers (ARBs), beta2-agonists, centrally acting sympatholytics, direct acting vasodilators, endothelin receptor antagonists, ganglionic blockers, nitrodilators, phosphodiesterase inhibitors and renin inhibitors.

In some embodiments, the adjuvant which promotes vasodilation is a calcium channel blocker. "Calcium channel blocker" refers to compounds that block calcium activity or inhibit the flow of calcium ions across the membrane of smooth muscle cells. This decreases intracellular calcium leading to a reduction in muscle contraction. In the heart, it results in a decrease in cardiac contractility. In blood vessels, it results in less contraction of the vascular smooth muscle and therefore increases arterial diameter—a phenomenon known as vasodilation. Classes of calcium channel blockers include dihydropyridine calcium channel blockers (amlodipine, aranidipine, azelnidipine, barnidipine, cilnidipine, clevidipine, efonidipine, felodipine, lacidipine, lercanidipine, manidipine, nicardipine, nifedipine, nilvadipine, nimodipine, nisoldipine, nitrendipine and pranidipine), phenylalkylamine calcium channel blockers (e.g. verapamil and gallopamil), and benzothiazepine calcium channel blockers (e.g. diltiazem).

In some embodiments, the calcium channel blocker is preferably a dihydropyridine calcium channel blocker. Exemplary dihydropyridine calcium channel blockers include nimodipine, amlodipine and nifedipine.

In accordance with the present invention, the maximum concentrations of the adjuvant which promotes vasodilation used therein is not toxic. In some embodiments, the maximum concentrations of the adjuvant which promotes vasodilation (e.g. calcium channel blocker) is usually less than 1 µM; preferably less than 0.7 µM; more preferably less than 0.5 µM. For example, when the calcium channel blocker, verapamil is used as an adjuvant which promotes vasodilation in accordance with the present invention, the maximum dosage would not reach 360 mg per day for oral treatment, or 180 mg in extended-release tablets. Lethal plasma concentrations of verapamil have been reported to be as low as 1.2 µM (Kinoshita, et al., *Forensic Science International* 2003, 133 107-112).

In accordance with the present invention, there are also provided unit dosage forms for the treatment of malaria, said dosage form comprising a therapeutically effective amount of an anti-malaria drug, its pharmacologically acceptable salt, or a hydrate or solvate, and a therapeutically effective amount of an adjuvant which promotes vasodilation which promotes vasodilation, its pharmacologically acceptable salt, or a hydrate or solvate. The therapeutically effective and non-toxic amount of the adjuvant which promotes vasodilation in the dosage forms may be in the range of about 20 mg/dose to about 90 mg/dose or about 7.5 µg/Kg/hour to about 30 µg/Kg/hour. The therapeutically effective amount of said anti-malaria drug in the dosage forms may be in the range of about 10 mg/dose to about 1500 mg/dose or about 1 mg/Kg/hour to about 10 mg/Kg/hour.

Exemplary dosages for anti-malaria drugs for treating severe malaria are listed below.

| Anti-malaria drug | Dosage |
| --- | --- |
| Quinine | IV or IM: 5-10 mg/kg/dose |
| Artemisinin | suppositories: 20-1,200 mg/dose |

-continued

| Anti-malaria drug | Dosage |
|---|---|
| Artesunate | IV or IM: 1-3 mg/kg/dose; 60-120 mg/dose; suppositories: 200 mg/dose |
| Artemether | IV or IM: 1.6-4 mg/kg/dose; 10-200 mg/dose |

IV: intravenous.
IM: intramuscular.

Exemplary dosages for anti-malaria drugs for treating uncomplicated malaria are listed below.

| Anti-malaria drug | Dosage |
|---|---|
| Quinine | 125-1,000 mg |
| Artesunate | 600 mg/dose |
| Mefloquine | 500-1,500 mg single dose |

The therapeutically effective and non-toxic amount of the exemplary adjuvant which promotes vasodilation, nimodipine, may be in the range of about 20 mg to about 90 mg per dose or about 7.5 µg/Kg/hour to about 30 µg/Kg/hour.

As used herein, the terms "therapeutic" and/or "effective" amounts mean an agent utilized in an amount sufficient to treat, combat, ameliorate, prevent or improve a condition or disease of a subject. A therapeutically effective amount can be readily determined by the attending physician, as one skilled in the art, by the use of known techniques and by observing results obtained under analogous circumstances. In determining the therapeutically effective amount or dose, a number of factors are considered by the attending physician, including, but not limited to: the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the use of concomitant medication; and other relevant circumstances. "Subject" refers to mammals and includes humans and non-human mammals.

In yet other embodiments, the composition further comprises a pharmaceutically acceptable carrier. In certain embodiments, the compositions are formulated for oral, intravenous (IV), intramuscular (IM), intraperitoneal (IP) or nasogastric tube administration.

The phrase "pharmaceutically acceptable carrier" is art-recognized, and includes, for example, pharmaceutically acceptable materials, compositions or vehicles, such as a liquid or solid filler, diluent, solvent or encapsulating material, involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

For example, for purposes of intraperitoneal administration, anti-malarial drug (e.g. artemether) and a adjuvant which promotes vasodilation (e.g. nimodipine) may be incorporated into a solution or a suspension. The amount of anti-malarial drug or adjuvant which promotes vasodilation in such compositions is such that a suitable dosage will be obtained. The solution or suspension may also include the following components: a sterile diluent, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity or osmolarity, such as sodium chloride or dextrose. The preparation may be enclosed in ampoules, disposable syringes or multiple dose vials made of glass or plastic.

In some embodiments, the compositions are formulated for intravenous administration. The compositions may comprise the anti-malaria drug and the adjuvant which promotes vasodilation at a weight ratio in the range of about 7:1 to about 1500:1. For example, A 7.5-150 µg/Kg/dose of nimodipine may be used in combination with about 1.6-4 mg/Kg/dose of artemether or about 5-10 mg/Kg/dose of quinine for IV administration.

The compositions may be formulated for oral administration. For example, anti-malaria drug (e.g. artemether) and adjuvant which promotes vasodilation (e.g. nimodipine) may be formulated with an inert diluent, typically an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, waters, chewing gums, and the like. The amount of the compounds employed in various embodiments of the present invention will be such that a suitable dosage will be provided in the administered amount.

In some embodiments, the compositions are formulated for oral administration. The compositions may comprise the anti-malaria drug and the adjuvant which promotes vasodilation at a weight ratio in the range of about 1:1 to about 75:1. For example, A 20-90 mg/dose of nimodipine may be used in combination with about 125 to 1,500 mg/dose of artemether or about 20-1200 mg/dose of artesunate for oral administration.

Tablets, pills, capsules, troches and the like may contain the following ingredients: a binder, such as micro-crystalline cellulose, gum tragacanth or gelatin; an excipient, such as starch or lactose; a disintegrating agent, such as alginic acid, Primogel, corn starch and the like; a lubricant, such as magnesium stearate or Sterotes; a glidant, such as colloidal silicon dioxide; a sweetening agent, such as sucrose, saccharin or aspartame; or flavoring agent, such as peppermint, methyl salicylate or orange flavoring. When the dosage unit form is a capsule it may contain, in addition to compounds comprising embodiments of the present invention, a liquid carrier, such as a fatty oil. Other dosage unit forms may contain other materials that modify the physical form of the dosage unit, for example, as coatings. The coating(s) can be formulated for immediate release, delayed/enteric release or sustained release of the second pharmaceutical active in accordance with methods well known in the art. For example, a coating for immediate release is commonly used as a moisture barrier, and for taste and odor masking. Rapid breakdown of the coating in gastric media will lead to effective disintegration and dissolution. Thus, tablets or pills may be coated with sugar, shellac or other enteric coating agents. A syrup may contain, in addition to the active compounds, sucrose as a sweetening agent and preservatives, dyes, colorings and flavors. Materials used in preparing these compositions should be pharmaceutically pure and non-toxic in the amounts used.

The dosage form of the present invention may be either immediate or controlled release. For example, an immediate release form may comprise one or more pharmaceutically acceptable excipients including, but not limited to, one or more of microcrystalline cellulose, hydroxypropylcellulose, starch, lactose monohydrate, anhydrous lactose, talc, colloidal silicon dioxide, providone, citric acid, poloxamer, sodium starch glycolate, stearic acid, and magnesium stearate.

Controlled release can be achieved in the formulations by several mechanisms known in the art. For example, pH sensitive polymer or co-polymer can be used which when applied around the drug matrix functions as an effective barrier to release of active at certain pH range. An alternative to a pH sensitive polymer or co-polymer is a polymer or co-polymer that is non-aqueous-soluble. The extent of resistance to release, for example, in the gastric environment can be controlled by coating with a blend of the non-aqueous-soluble and a aqueous soluble polymer. In this approach neither of the blended polymers or co-polymers are pH sensitive. One example of a pH sensitive co-polymer is the Eudragit® methacrylic co-polymers, including Eudragit® L 100, S 100 or L 100-55 solids, L 30 D-55 or FS 30D dispersions, or the L 12,5 or S 12,5 organic solutions. The polymers may be applied to a tablet for example, by spray coating (as a thin film), by compression coating or other suitable procedures. Polymer(s) may be applied over the surface of the capsule or applied to microparticles of the drug, which may then be encapsulated such as in a capsule or gel.

A sustained release film coat may be used for the invention compositions including a water insoluble material such as a wax or a wax-like substance, fatty alcohols, shellac, zein, hydrogenated vegetable oils, water insoluble celluloses, polymers of acrylic and/or methacrylic acid, and any other slowly digestible or dispersible solids known in the art.

Other means known in the art such as a swellable hydrogel may be used to delay release (an osmotic pump system). The swellable hydrogel takes up moisture after administration. Swelling of the gel results in displacement of the drug from the system for absorption. The timing and rate of release of the drug depend on the gel used, and the rate at which moisture reaches the gel, which can be controlled by the size of the opening in the system through which fluid enters. See Drug Delivery Technologies online article Dong et al., "L-OROS® SOFTCAP™ for Controlled Release of Non-Aqueous Liquid Formulations.

In accordance with the present invention, there are provided methods for the treatment of malaria in a mammal comprising simultaneously or serially administering to said mammal a therapeutically effective amount of an anti-malaria drug, its pharmacologically acceptable salt, or a hydrate or solvate, and a therapeutically effective amount of an adjuvant which promotes vasodilation, its pharmacologically acceptable salt, or a hydrate or solvate.

"Treating" or "treatment" of a disease in a patient refers to (1) preventing the disease from occurring in a patient that is predisposed to contacting diseases or has been exposed but does not yet display symptoms of the disease; (2) inhibiting the disease or arresting its development; or (3) ameliorating or causing regression of the disease.

In some embodiments, the methods may comprise separately administering an adjuvant which promotes vasodilation and an anti-malaria drug in close temporal proximity. In other embodiments, the methods may comprise serially administering first the adjuvant which promotes vasodilation and then the anti-malaria drug or serially administering first the anti-malaria drug and then the adjuvant which promotes vasodilation. In some embodiments, the adjuvant which promotes vasodilation is a vasodilator. In some embodiments, the adjuvant which promotes vasodilation is a calcium channel blocker. The calcium channel blocker may be a dihydropyridine calcium channel blocker. The method may comprise administering a dosage of about 20 mg to about 90 mg of the dihydropyridine calcium channel blocker to the mammal orally every 4 hours. The dihydropyridine calcium channel blocker may be nimodipine of which a dosage of about 20 mg/dose to about 90 mg/dose may be administered to the mammal orally every 4 hours.

In some embodiments, the anti-malaria drug employed according to invention methods is selected from the group consisting of quinine, mefloquine, amodiaquine, chloroquine, halofantrine, atovaquone-proguanil, sulfadoxine-pyrimethamine, artemisinin, artemether, artesunate and arteether; preferably artemether. A dosage of about 10 mg to about 1500 mg of the anti-malaria drug may be administered to the mammal per day. For example, a dosage of about 10 mg/dose to about 200 mg/dose of the artemether may be administered to the mammal per day.

In some embodiments, the present invention provides uses of an anti-malaria drug, its pharmacologically acceptable salt, or a hydrate or solvate and an adjuvant which promotes vasodilation, its pharmacologically acceptable salt, or a hydrate or solvate, in the preparation of a medicament for the treatment of malaria in a mammal.

The present invention also provides methods of modulating vasoconstriction or vascular collapse caused by conditions associated with malaria, comprising: co-administering a therapeutically effective amount of an adjuvant which promotes vasodilation, its pharmacologically acceptable salt, or a hydrate or solvate with an anti-malaria drug.

In accordance to the present invention, it is shown that the brain microcirculatory physiology is severely comprised during murine CM, with arteriolar blood flow decreasing by more than 60% at the time of CM manifestation, confirming that ischemia plays a significant role in murine CM (Penet, et al., *J Neurosci.* 2005, 25, 7352-7358; Sanni, et al., *Am J Pathol.* 2001, 159, 1105-1112). Since vasoconstriction and vascular collapse are associated with ischemia, a therapeutically effective amount of an adjuvant which promotes vasodilation can be administered to modulate vasoconstriction or vascular collapse caused by conditions associated with malaria, especially CM. In some embodiments, the adjuvant which promotes vasodilation comprises a vasodilator or calcium channel blocker. For example, when 4 mg/Kg of nimodipine was administered to PbA-infected mice with an implanted cranial window, arteriolar blood flow increased by about 50% after 30 minutes of injection. The effect in inducing vasodilation in murine CM pathogenesis also exhibits marked impact on the survival rated of mice with CM (60-66.6% survival).

In some embodiments, the modulating vasoconstriction or vascular collapse according to invention methods increases cerebral blood flow, in particular increases in pial blood flow. In accordance with the present invention, it was shown that the reaction of pial arterioles in murine CM dilate in response to the adjuvant which promotes vasodilation (e.g. nimodipine).

EXAMPLES

The following examples are provided to illustrate certain aspects of the present invention and to aid those of skill in the art in practicing the invention. These examples are not intended to limit the scope of the invention.

Example 1

Parasite, Infection and Clinical Assessment

All protocols were approved by the La Jolla Bioengineering Institutional Animal
Care and Use Committee. Eight to 10-week old C57B1/6 mice (Jackson Laboratories, ME) were inoculated intraperitoneally with $1 \times 10^6$ *Plasmodium berghei* ANKA (PbA) parasites expressing the GFP protein (obtained from MR4-NIH, deposited by C J Anders and A Waters). Parasitemia, body weight and rectal temperature were checked daily from day 4. A motor behavior assessment modified from the SHIRPA protocol was used to determine the clinical status of the animals (Lackner, et al., *Neuropathol Appl Neurobiol*. 2006, 32, 177-188). Five tests were performed: transfer arousal, locomotor activity, tail elevation, wire maneuver and righting reflex. For each test, mice received an individual score, and the sum of scores was used to create a composite score.

Example 2

Intravital Microscopy

The closed cranial window model (See Mostany, et al., *J Vis Exp*. 2008, 15, pii: 680) was used. Briefly, mice were anesthetized with ketamine-xylazine, the head held on a stereotaxic frame, the scalp cut off and a 3-4 mm diameter skull opening was made in the left parietal bone using a surgical drill. The exposed area was covered with a 5 mm glass cover slip glued with dental acrylic. Carprofen and ampicillin were given for 3-5 days to prevent pain, inflammation and infection. Two weeks after surgery, mice were lightly anesthetized with isoflurane (4% for induction, 1-2% for maintenance) and held on a stereotaxic frame. A panoramic picture of the window was taken and then mice were transferred to an intravital microscope stage (customized McBain, San Diego, Calif.). Body temperature was maintained using a heating pad. Using water-immersion objectives (20x), blood vessel images were captured (COHU 4815, San Diego, Calif.) and recorded on video-tape. An image shear device (Image Shear, Vista Electronics, San Diego, Calif.) was used to measure baseline vessel diameters (D) and RBC velocities (V) were measured off line by cross correlation (Photo Diode/Velocity Tracker Model 102B, Vista Electronics, San Diego, Calif.). Measurements of 6-10 pial venules (diameter range: 22-80 μm, velocity range: 2-4 mm/s) and 2-6 pial arterioles (diameter range: 18-70 μm, velocity range: 3-6 mm/s) were performed in each animal, and blood flow (Q) in each individual vessel was calculated using the equation: $Q=V \times (D/2)_2$.

The next day mice were inoculated intraperitoneally with $1 \times 10^6$ PbA-GFP pRBC. The intravital microscopy procedure was repeated daily from day 4 of infection until the mice died or were euthanized. Non-infected control mice were submitted to the same procedures. To enhance imaging of the vascular network (including poorly perfused vessels), animals with clinical signs of cerebral malaria (CM) were infused intravenously with albumin-FITC (Molecular Probes, Irvine, Calif., 1 mg/kg). Adherent and rolling leukocytes were visualized by anti-CD45-TxR antibodies (CalTag, Carlsbad, Calif.), also infused intravenously. To evaluate the effect of nimodipine on pial blood flow, the same procedure was undertaken and PbA-infected mice with clinical CM and non-infected controls were imaged, parameters measured and then these mice were injected with artemether plus nimodipine at 4 mg/kg (as described in Example 3) and measurements were repeated at 30, 60 and 120 minutes. CM was defined as the presentation of one or more of the following clinical signs of neurological involvement: ataxia, limb paralysis, poor righting reflex, seizures, roll-over, coma.

Example 3

Treatment

PbA-infected mice presenting poor righting reflex, hypothermia and/or other clinical signs of neurological involvement such as ataxia, limb paralysis, seizures and/or roll-over were treated with artemether (Artesiane, Dafra Pharma, Belgium, a kind gift of Dr Alberto Moreno, Emory University, Atlanta, Ga.) given IP at 50 mg/kg, in combination with nimodipine (Sigma, St Louis, Mo.) or vehicle (ethanol:polyethyleneglycol (PEG) 400:saline in 1:1:8 v/v). Nimodipine was dissolved in ethanol (EMD, N.J.), dispersed with polyethyleneglycol 400 (PEG, Sigma) and then saline was added (1:1:8 v/v) and mixed thoroughly. This solution was administered intraperitoneally in three different doses: 1.3 mg/kg, 4 mg/kg and 12 mg/kg. Artemether was given daily for 5 days, and nimodipine or vehicle were given at 0, 12, 24 and 36 hours. Parasitemia, motor behavior and rectal temperature were checked at each timepoint and daily afterwards. After treatment, parasitemia was checked by microscopical examination of Giemsa-stained blood smears to differentiate viable from dead parasites.

Example 4

Statistical Analysis

Statistical analyses were performed using the Student's T test with Mann-Whitney correction when comparing two groups, analysis of variance (ANOVA) with Kruskall-Wallis post-hoc analysis when comparing more than two groups, and survival curves were compared with a nonparametric log-rank test, using the Graphpad Prizm software (GraphPad Software Inc., La Jolla, Calif.). A P value<0.05 was considered significant. Reported data are the mean±s.e.m. unless otherwise indicated.

Figure 1A:
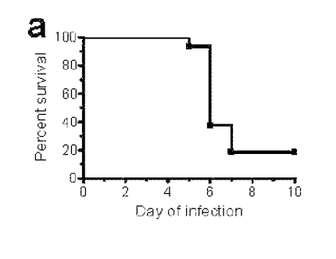
FIGS. 1a-1h. show that PbA infection leads to decreased blood flow in pial vessels. Cumulative survival (FIG. 1a), course of parasitemia (FIG. 1b) and rectal temperature (FIG. 1c) in PbA-infected mice that did (n=13) or did not (n=3) develop cerebral malaria (CM) and in uninfected control mice (n=9). Rectal temperature was lower in mice with CM than in uninfected controls (p=0.0004). Arteriolar (FIG. 1d) and venular (FIG. 1e) blood flow in PbA-infected mice with or without CM and in control mice. Results are expressed as the percentual change in relation to baseline measurements performed before infection. Flow was significantly decreased on day 6 in mice that developed CM (arteriolar: p=0.0003; venular: p=0.0003). Mice with CM (irrespective of the day of clinical presentation) presented significantly decreased arteriolar blood flow (FIG. 1f; p<0.0001), diameters (FIG. 1g; p=0.0079) and RBC velocities (FIG. 1h, p=0.007) than uninfected control mice. Data are the mean±s.e.m.
Figure 1B:
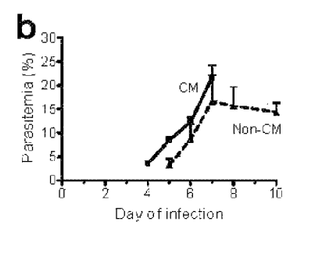
Figure 1C:
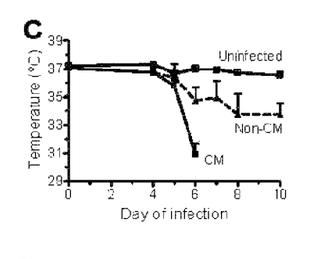
Figure 1D:
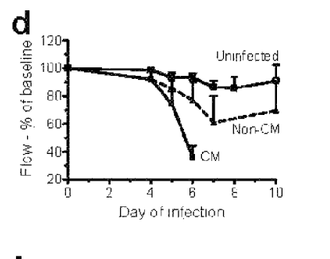
Figure 1E:
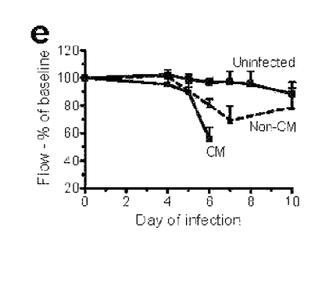
Figure 1F:
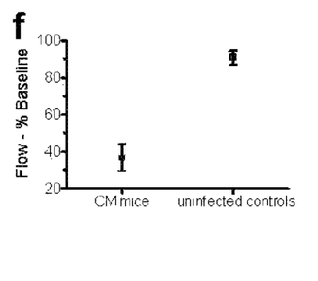
Figure 1G:
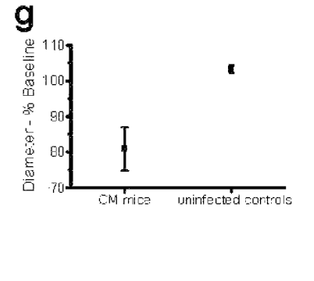
Figure 1H:
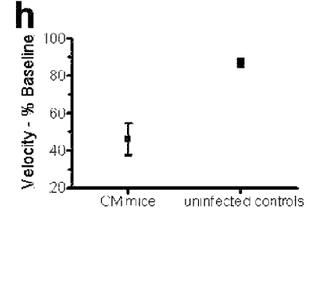

Mice with an implanted cranial window and infected with PbA presented an overall CM incidence of 81% (n=16, three separate experiments), deaths occurring on days 5-7 (FIG. 1*a*) with parasitemias between 10 and 30% (FIG. 1*b*). Infected mice developed hypothermia, more severe in CM mice (FIG. 1*c*). Marked decreases in arteriolar and venular blood flows were observed during infection, particularly in mice presenting clinical signs of CM (FIGS. 1*d*, 1*e*, and 1*f*), due to both vessel constriction and lower RBC velocities (FIGS. 1*g* and 1*h*). Non-infected control mice showed variations within 15% of baseline (FIG. 1*d-h*).

Figures 2A, 2B, 2C, 2D, 2E, 2F, 2G, 2H:
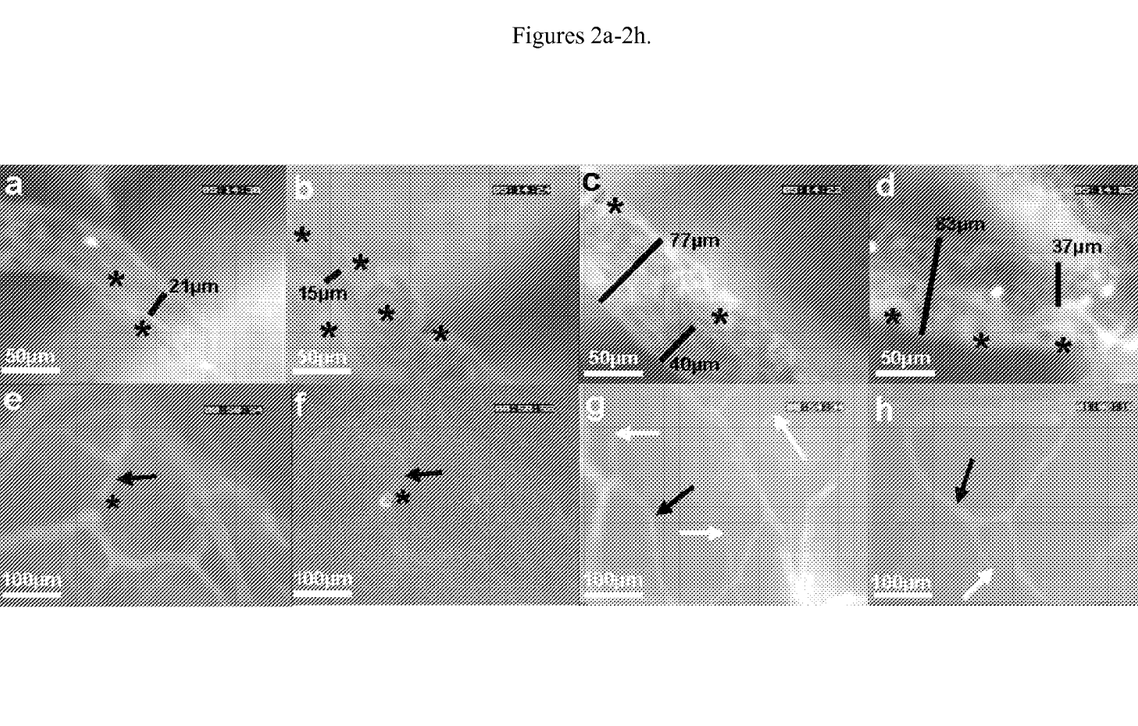
FIGS. 2a-2h. illustrate that CM is associated with impaired perfusion in pial vessels. Four consecutive sections (FIG. 2a-2d) of the same venule showing how adherent leukocytes can cause marked reduction in luminal diameters and impair perfusion (more detailed, dynamic view is available at the supplementary video 3). Asterisks show adherent leukocytes. The luminal venule diameter in specific sections is shown (black bars with the respective diameter value); note the large variations in diameter mostly due to adherent leukocytes, and a site of major constriction in FIG. 2b with apparent damage of the vessel structure. Bright spots in FIG. 2a and FIG. 2d are flowing fluorescent PbA-GFP pRBC. Adherent leukocytes can completely block blood flow in small venules (FIG. 2e, 2f): two consecutive frames showing vessels stained with albumin-FITC, one of them is non-perfused (arrow) blocked by an adherent leukocyte (asterisk) (FIG. 2e) and the same area showing the leukocyte stained with anti-CD45TxR antibodies (FIG. 2f) (see dynamic view in supplementary video 6). Collapse of non-perfused small vessels (FIG. 2g, FIG. 2h): disappearance of small vessels with no flow (white arrows), and associated non-flowing vessels (black arrows).
Figures 3A, 3B, 3C, 3D, 3E, 3F, 3G, 3H, 3I, 3J, 3K, 3L:
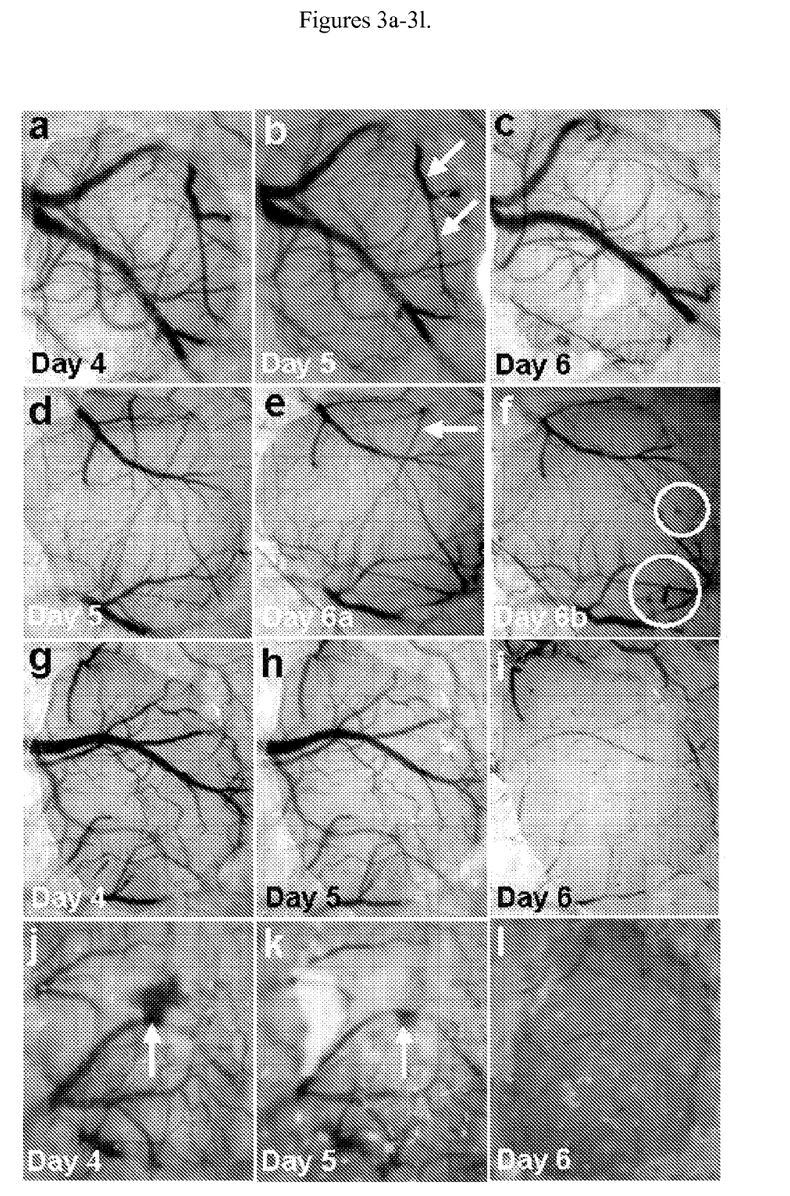
FIGS. 3a-3l demonstrate that CM is associated with vascular collapse. Collapse of a major pial vessel and branches (arrows) on day 6 of infection (FIG. 3a-3c). Collapse of two branches (arrows) of a vessel and microhemorrhages (encircled) (FIG. 3d-3f); pictures of day 6a and b were taken with a 3-hour interval, during which the mouse developed clinical CM. Collapse of virtually the entire pial vascular network under the cranial window on day 6 of infection (FIG. 3g-3i). Collapse of the vascular network under the window on day 6 following a major hemorrhage (arrow) on days 4 and 5 (FIG. 3j-3l).

Infected mice without CM presented similar but less pronounced disturbances, with delayed parasitemia, higher core temperature and moderate decreases in blood flow as compared to mice with CM. In many venules of mice with CM the large number of adherent leukocytes functioned as barriers to blood flow by causing marked reductions in luminal diameter (FIG. 2*a-d*). Sequestered pRBC were rarely observed and, in such cases, the trapped cells were usually attached to the surface of an endothelium-adherent leukocyte, confirming previous observations by histology (Martins, et al., Int *J. Exp. Pathol.* 2009, 90, 119-130). RBC velocities were observed to be heterogeneous, with some larger vessels presenting sluggish RBC velocities and non-perfused feeding vessels. Capillaries and smaller venules were frequently non-perfused and in some cases adherent leukocytes were found to obstruct the lumen (FIGS. 2*e* and 2*f*). Non-perfused vessels eventually collapsed (FIGS. 2*g* and 2*h*). A striking feature observed in mice with CM was the collapse of large pial vessels (FIG. 3*a*, 3*c*, 3*d-f*) or even of a microvascular network (FIG. 3*g-i*), which was eventually preceded by the occurrence of hemorrhage in a major vessel (FIG. 3*j-l*). This phenomenon was observed in 5/13 (39%) of the CM animals (3 mice with one or few vessels collapsed and 2 mice with vascular network collapse), and in none of the control or non-CM mice. Vascular collapse was preceded by or coincident with intense vasoconstriction, with a 32% decrease in overall arteriolar diameter in relation to baseline (p=0.0058) in the affected animals.

Figure 4A:
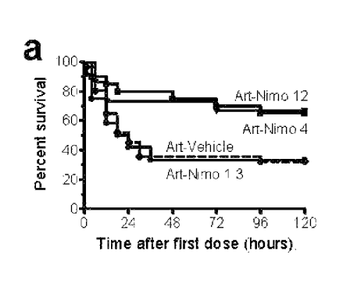
FIGS. 4a-4h present the results that Nimodipine improves the death-rescuing capacity of artemether on mice with established CM. Cumulative survival (FIG. 4a) of PbA-infected mice presenting clinical CM and treated with artemether-nimodipine (1.3 mg/kg, n=12; 4 mg/kg, n=20; and 12 mg/kg, n=15) or artemether-vehicle (n=31). A total of nine experiments were conducted. Survival was significantly increased in mice treated with 4 mg/kg (p=0.0217) and 12 mg/kg (p=0.0474), but not with 1.3 mg/kg. Mice treated with artemether plus vehicle or artemether plus different concentrations of nimodipine presented no significant differences in clinical and parasitological status at the time of first dose (FIG. 4b-4c): mean composite motor score (FIG. 4b, controls: 22.3±0.236), rectal temperature (FIG. 4c, controls: 36.7±0.156) and parasitemia (FIG. 4d). Survivor mice treated with artemether plus nimodipine (n=20) presented faster clinical recovery than survivor mice treated with artemether-vehicle (n=9) (FIG. 4e), with significantly higher scores at 48 (p=0.0402) and 72 (p=0.0238) hours. Efficacy of artemether treatment: parasitemia decreased fast after artemether administration in mice treated with nimodipine or vehicle (FIG. 4f). Nimodipine increases blood flow in CM mice through vasorelaxation: administration of nimodipine at 4 mg/kg IP caused an increase in arteriolar blood flow in mice with clinical CM (n=3) and in uninfected control mice (n=3) (FIG. 4g); increase in arteriolar blood flow was due to a sustained increase in vascular diameter (FIG. 4h). Data are the mean±s.e.m.
Figure 4B:
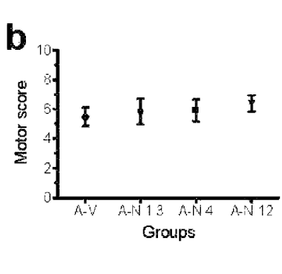
Figure 4C:
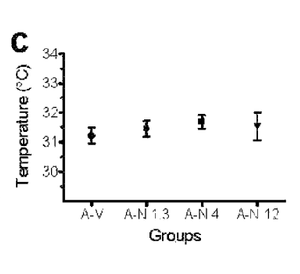
Figure 4D:
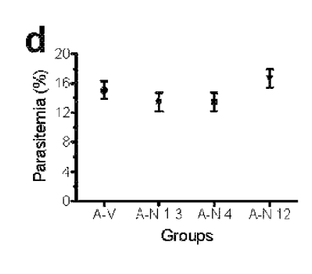
Figure 4E:
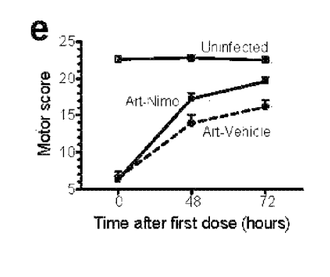
Figure 4F:
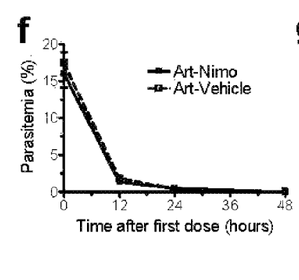

When the adjunctive administration of nimodipine at 4 and 12 mg/kg, but not 1.3 mg/kg was employed, it was able to rescue twice as many (60-66.6% survival) mice from CM and death than did artemether plus vehicle (32.2% survival) (FIG. 4*a*). There were no significant differences in the clinical and parasitological status of mice randomly assigned to the different treatment groups (FIG. 4*b-d*). In addition, mice treated with nimodipine at 4 mg/kg but succumbing showed prolonged survival, with half of the deaths occurring over a period of 48 to 120 hours after the first dose, whereas in the vehicle-treated group 95.2% of deaths occurred in the first 36 hours. The survivor mice treated with nimodipine showed faster recovery than did survivor mice treated with vehicle, with significantly higher motor scores at 48 and 72 hours (FIG. 4*e*). There was no difference in the rate of parasite clearance in the nimodipine and vehicle groups (FIG. 4*f*). Within one week of treatment, all but one (97.2%) of the survivor mice in all groups presented apparent full recovery from the neurological syndrome, only one mouse showing evidence of sequelae three weeks after treatment (head slightly leaned to the left).

Figure 4G:
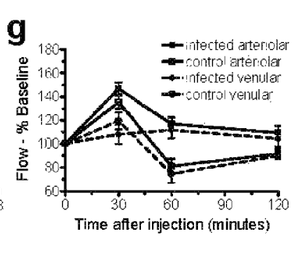
Figure 4H:
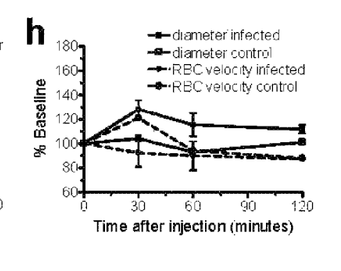

When PbA-infected mice with an implanted cranial window and presenting clinical CM were given nimodipine 4 mg/kg IP, arteriolar blood flow increased by about 50% after 30 minutes of injection, then decreased but remained above baseline after 2 hours (FIG. 4*g*). Vascular response in non-infected control mice was similar, but with a rebound at 60 minutes following the peak at 30 minutes. The increase in blood flow in mice with CM was due solely to a sustained increase in arteriolar diameters, since RBC velocities were even slightly decreased (FIG. 4*h*). These data indicates that the adjunctive effect of nimodipine was related to its vasorelaxation activity and ability to improve blood flow in the brain.

From the foregoing it will be appreciated that, although specific embodiments of the invention have been described herein for purposes of illustration, various modifications may be made without deviating from the spirit and scope of the invention claimed. Obviously, numerous modifications and variations of the present invention are possible in light of the above teachings. It is therefore to be understood that within the scope of the appended claims, the invention may be practiced otherwise than as specifically described herein.

What is claimed is:

1. A method for the treatment of cerebral malaria, said method comprising simultaneously or serially administering to said mammal a therapeutically effective amount of an artemisinin or an artemisinin derivative, and nimodipine in a therapeutically effective amount to promote vasodilation.

2. The method of claim 1 wherein the artemisinin derivative is selected from artesunate, artemether, and arteether.

3. The method of claim 1, comprising administering a single formulation comprising nimodipine and artemisinin or an artemisinin derivative.

* * * * *

UNITED STATES PATENT AND TRADEMARK OFFICE
CERTIFICATE OF CORRECTION

PATENT NO. : 9,737,478 B2
APPLICATION NO. : 12/881124
DATED : August 22, 2017
INVENTOR(S) : Leonardo Jose de Moura Carvalho and Pedro Cabrales It is certified that error appears in the above-identified patent and that said Letters Patent is hereby corrected as shown below:

On the Title Page

At item (73) Assignee:
Remove "National Institutes of Health (NIH), U.S. Dept. of Health and Human Services (DHHS), The United States of America NIH Division of Extramural Inventions and Technology Resources (DEITR), Washington, DC (US)"

And insert:
-- La Jolla Bioengineering Institute, La Jolla, CA (US) --

Signed and Sealed this
Third Day of October, 2017

Joseph Matal
*Performing the Functions and Duties of the*
*Under Secretary of Commerce for Intellectual Property and*
*Director of the United States Patent and Trademark Office*